(12) United States Patent
Tremblay et al.

(10) Patent No.: US 10,736,818 B2
(45) Date of Patent: Aug. 11, 2020

(54) RECONSTITUTION DEVICE WITH TIP CAP

(71) Applicant: Duoject Medical Systems Inc., Bromont (CA)

(72) Inventors: Yan Tremblay, Orford (CA); Mathieu Viens, Granby (CA)

(73) Assignee: Duoject Medical Systems Inc., Bromont, Quebec (CA)

( * ) Notice: Subject to any disclaimer, the term of this patent is extended or adjusted under 35 U.S.C. 154(b) by 317 days.

(21) Appl. No.: 15/932,597

(22) Filed: Mar. 20, 2018

(65) Prior Publication Data
US 2018/0207062 A1 Jul. 26, 2018

Related U.S. Application Data

(62) Division of application No. 13/262,000, filed on Dec. 17, 2014, now Pat. No. 9,956,142.

(51) Int. Cl.
*A61J 1/20* (2006.01)
*A61M 5/34* (2006.01)
(Continued)

(52) U.S. Cl.
CPC ............ *A61J 1/2096* (2013.01); *A61M 5/343* (2013.01); *A61J 1/201* (2015.05); *A61J 1/2051* (2015.05);
(Continued)

(58) Field of Classification Search
CPC ...... A61J 1/2096; A61J 1/2093; A61J 1/2089; A61J 1/201; A61J 1/2051; A61J 1/2055;
(Continued)

(56) References Cited

U.S. PATENT DOCUMENTS

| | | | |
|---|---|---|---|
| 6,258,078 B1 * | 7/2001 | Thilly | A61J 1/2096 604/411 |
| 9,039,047 B2 * | 5/2015 | Imai | A61J 1/2089 285/402 |

(Continued)

*Primary Examiner* — Philip R Wiest
(74) *Attorney, Agent, or Firm* — Eric Fincham

(57) ABSTRACT

A transfer member (128) comprising a housing (24) having a top, a side wall (26), an open bottom, the open bottom permitting insertion of a vial (12) within the housing, a piercing member (34) mounted within the housing (24), the piercing member (34) having a piercing tip (36) located at a bottom end thereof, the piercing member having an interior passageway formed therein, a connector (30) located on an exterior side of the top, a moveable member (40) mounted within the housing (24), the moveable member (40) being moveable from a first position wherein the moveable member (40) prevents access to the piercing tip (36) to a second position permitting access to the piercing tip when the vial is inserted in the housing, a transfer member (128), the transfer member (128) having first and second transfer member ends (131, 133) wherein the moveable member (40) and the housing (24) cause the moveable member (40) to rotate when the moveable member (40) moves upwardly upon insertion of the vial (12), the moveable member returning to a third locked position upon removal of the vial, the third locked position being such that a further vial cannot be inserted into the housing, the first transfer member end (131) being connectable to the second adaptor end (123), the second transfer member end (133) being arranged to receive a neck of a vial (130).

7 Claims, 14 Drawing Sheets

(51) Int. Cl.
 *A61M 5/315* (2006.01)
 *A61M 5/31* (2006.01)
(52) U.S. Cl.
 CPC .......... *A61J 1/2055* (2015.05); *A61M 5/3137* (2013.01); *A61M 5/31505* (2013.01)
(58) Field of Classification Search
 CPC . A61M 5/343; A61M 5/3137; A61M 5/31505
 See application file for complete search history.

(56) References Cited

U.S. PATENT DOCUMENTS

| | | | | |
|---|---|---|---|---|
| 2007/0079894 A1* | 4/2007 | Kraus | ...................... | A61M 5/32 |
| | | | | 141/319 |
| 2011/0074148 A1* | 3/2011 | Imai | ...................... | A61J 1/2089 |
| | | | | 285/308 |
| 2013/0072893 A1* | 3/2013 | Takemoto | ............. | A61J 1/2096 |
| | | | | 604/403 |

* cited by examiner

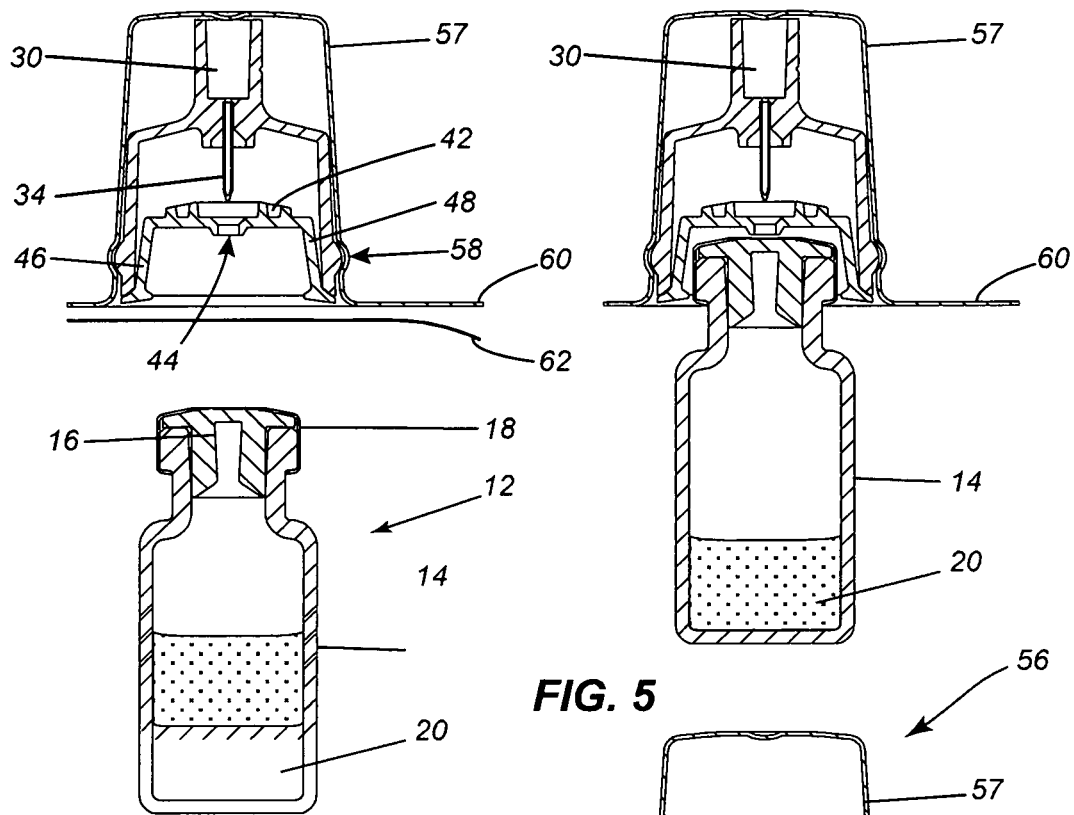
FIG. 4
FIG. 5
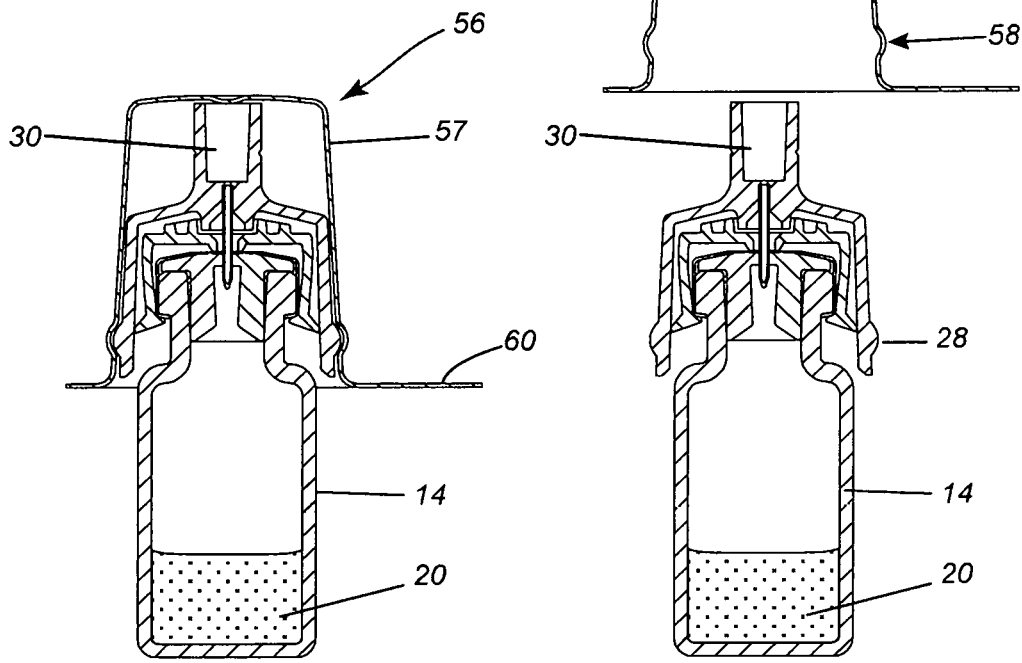
FIG. 6
FIG. 7

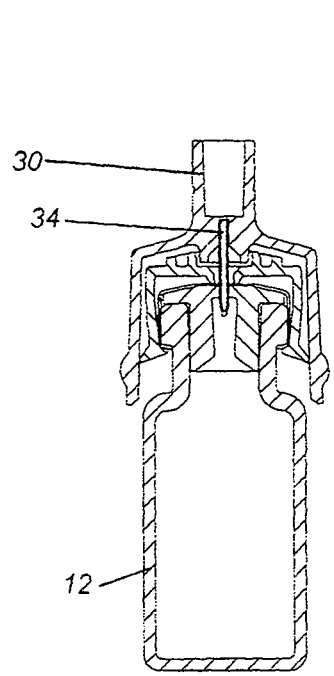
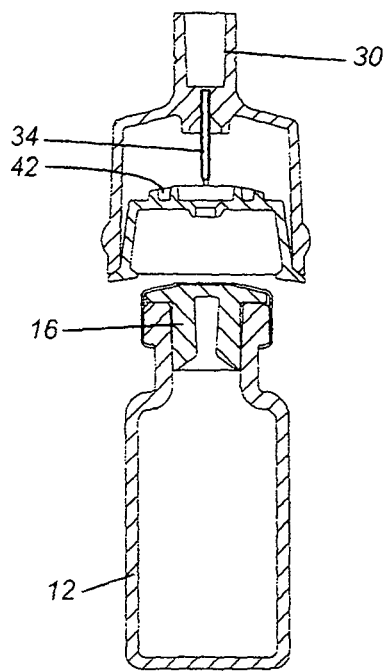
FIG. 13   FIG. 14
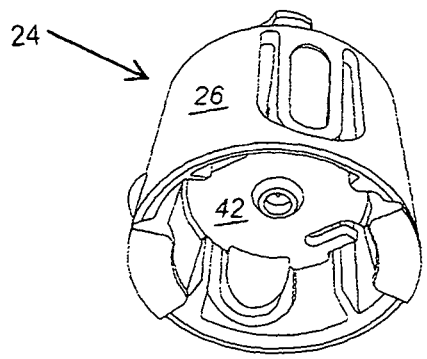
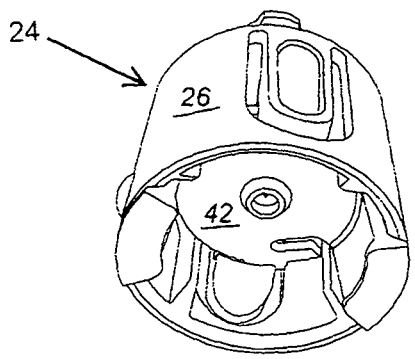
FIG. 15A   FIG. 16A
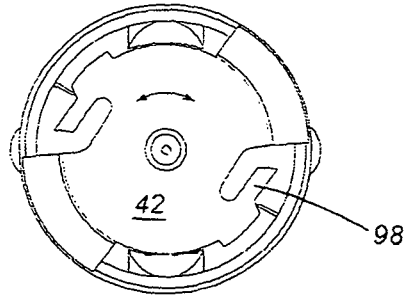
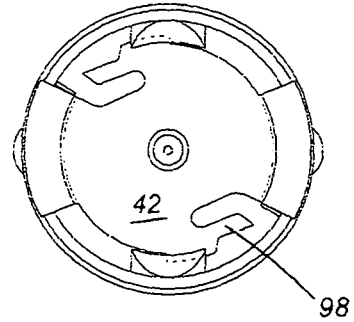
FIG. 15B   FIG. 16B

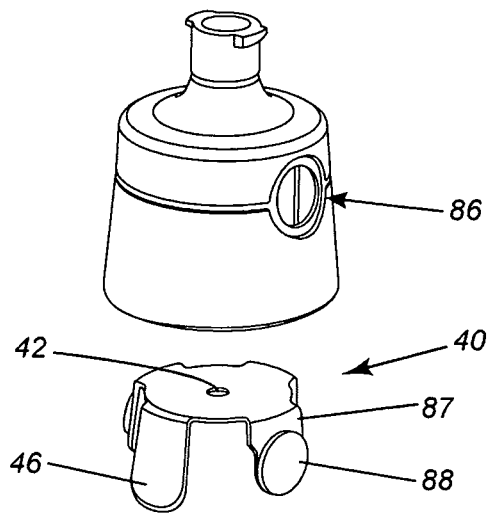
FIG. 17A
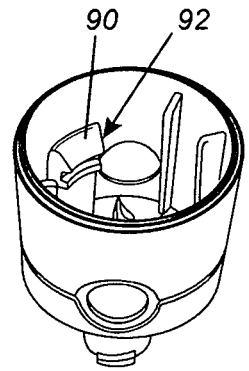
FIG. 17B
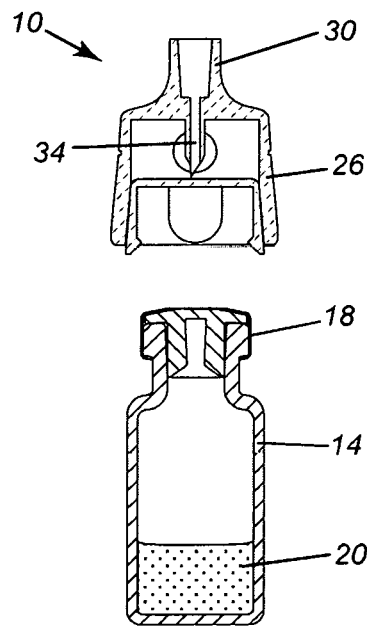
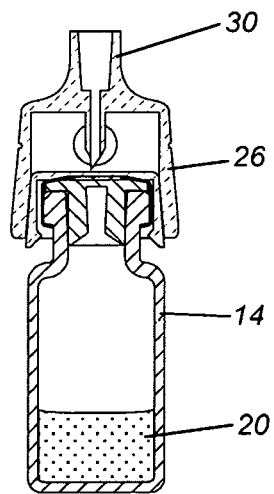
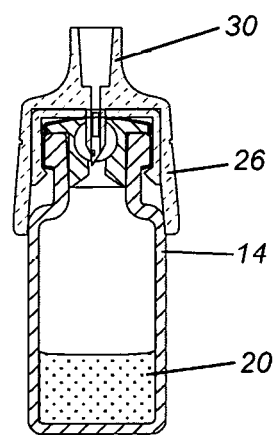
FIG. 17C   FIG. 17D   FIG. 17E

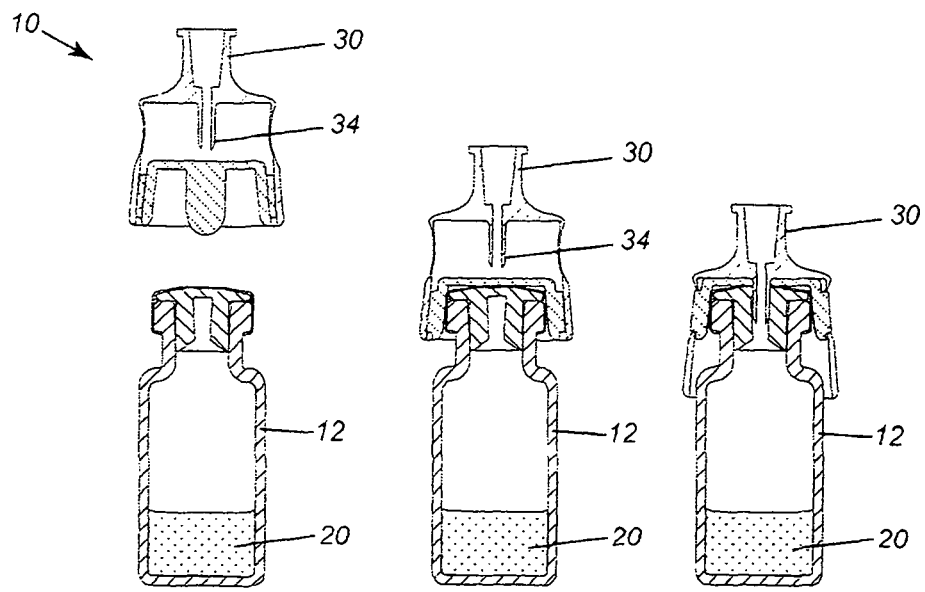
FIG. 17F  FIG. 17G  FIG. 17H
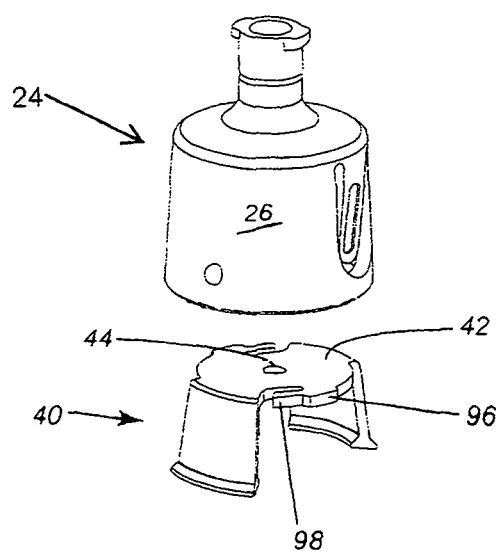
FIG. 18

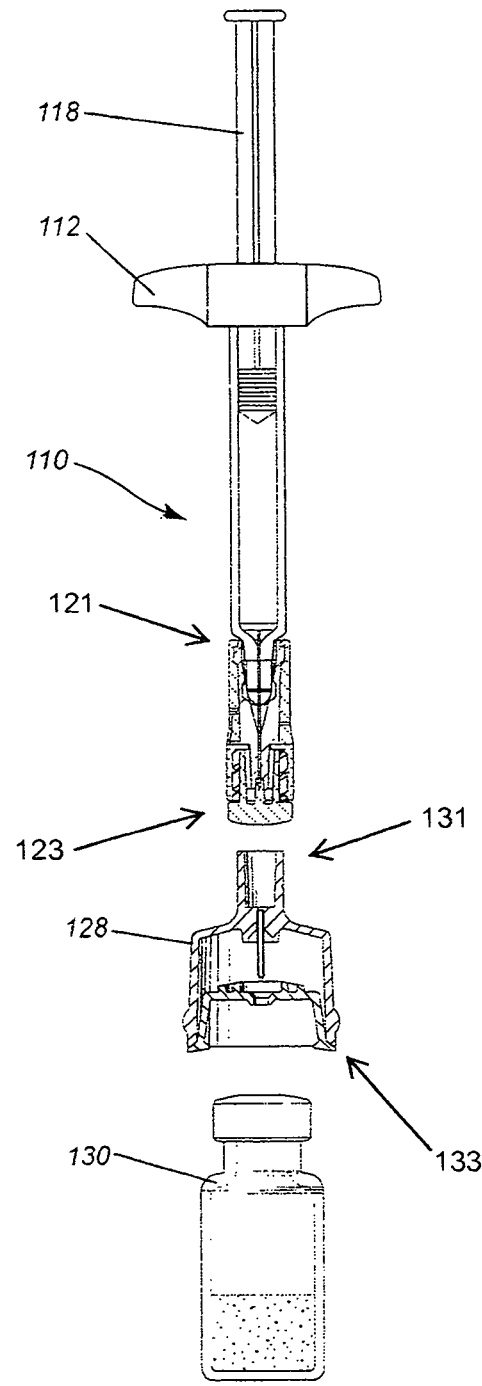
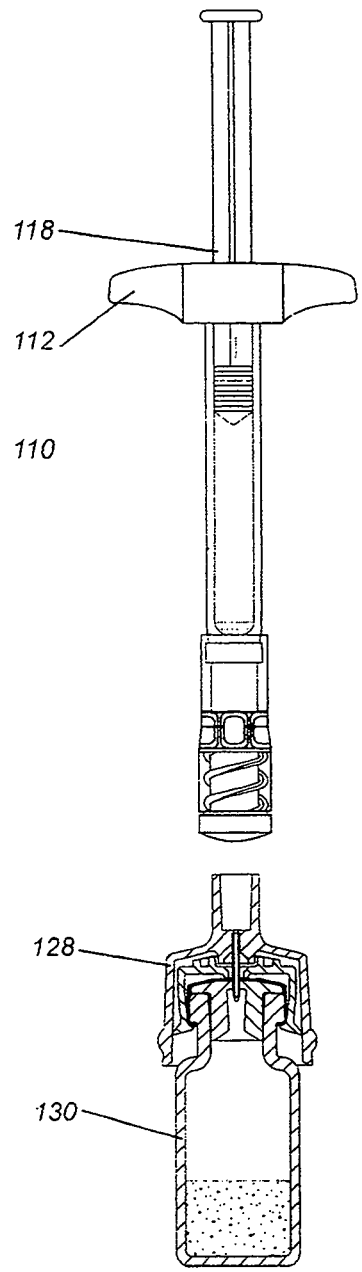
FIG. 21  FIG. 22

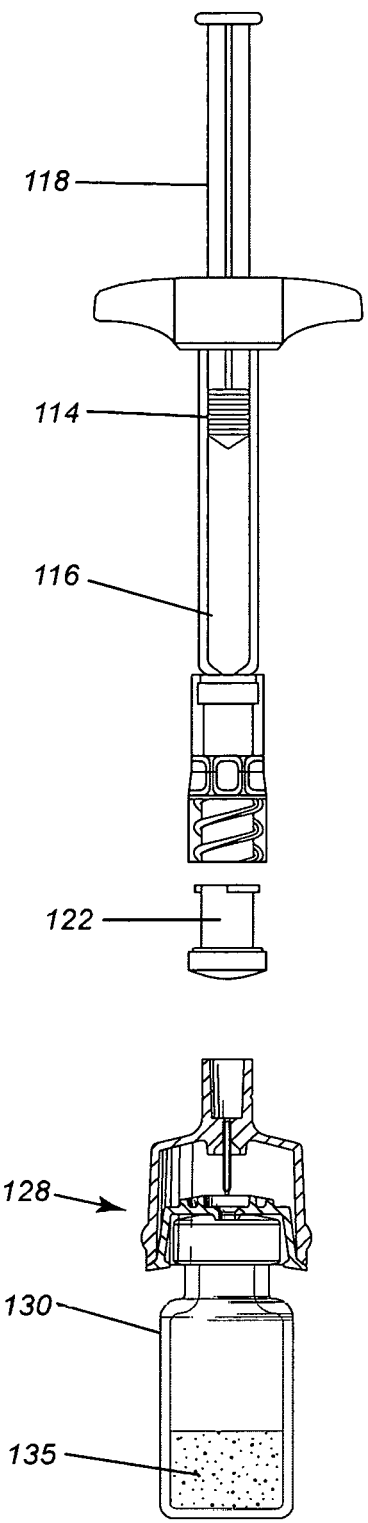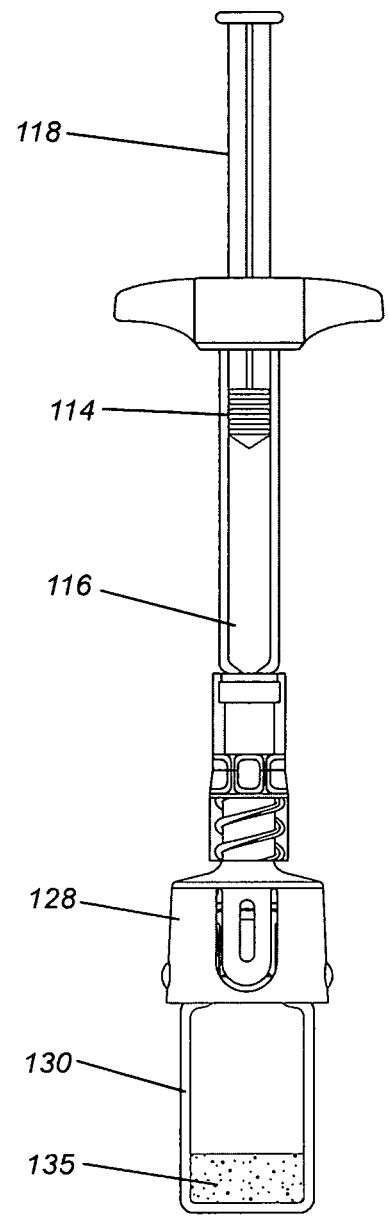
FIG. 23
FIG. 24

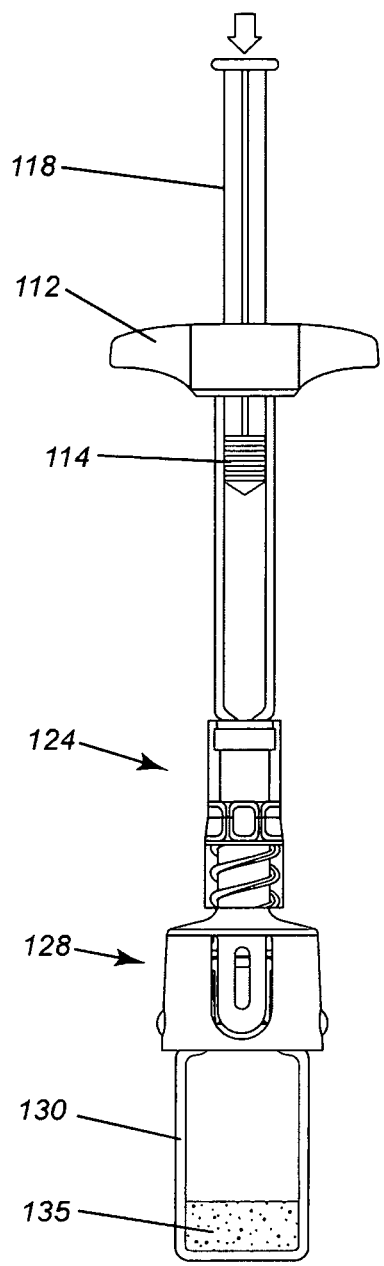
FIG. 25
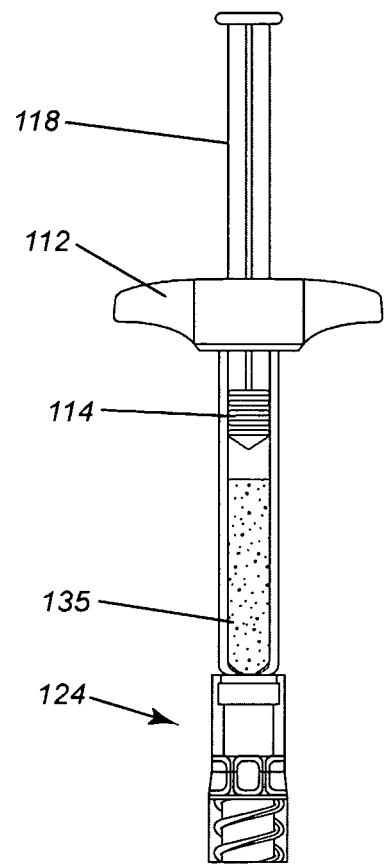
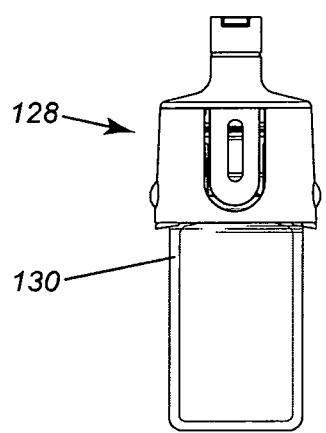
FIG. 26

RECONSTITUTION DEVICE WITH TIP CAP

This application is a Divisional of application Ser. No. 13/262,000 filed Dec. 17, 2014, the teachings of which are hereby incorporated by reference.

FIELD OF THE INVENTION

The present invention relates to a reconstitution system and more particularly, relates to a reconstitution system utilizing a syringe.

BACKGROUND OF THE INVENTION

Typically, a syringe is filled manually by aspirating a liquid pharmaceutical component from a pharmaceutical vial which has a penetrable closure. The syringe has a needle that penetrates the penetrable closure following which the syringe is typically filled by drawing air into the body of the syringe, aligning the needle with the vial's penetrable closure and inserting the needle through the penetrable closure into the vial. Subsequently, the vial is inverted and air is forced from the body of the syringe into the body of the vial. The plunger is then withdrawn to draw out the desired volume of the pharmaceutical component into the syringe and the needle is removed from the vial.

The above reconstitution is done since many pharmaceutical preparations must be distributed and sold as two separate components—typically a solid component and a liquid component. They are mixed just prior to administration. Actually, two or more components may each be liquid.

Typically, many procedures call for the needle to be removed from the syringe since there is danger of contamination of the needle. Furthermore, the silicone on the needle may be removed during the act of penetrating the vial.

SUMMARY OF THE INVENTION

It is an object of the present invention to provide an assembly for transferring the contents of the first container to a second container without contamination or alteration of the needle.

According to one aspect of the present invention, there is provided a transfer member comprising a housing having a top, a side wall, an open bottom, the open bottom permitting insertion of a vial within the housing, a piercing member mounted within the housing, the piercing member having a piercing tip located at a bottom end thereof, the piercing member having an interior passageway formed therein, a connector located on an exterior side of the top, a moveable member mounted within the housing, the moveable member being moveable from a first position wherein the moveable member prevents access to the piercing tip to a second position permitting access to the piercing tip when the vial is inserted in the housing, a transfer member, the transfer member having first and second transfer member ends wherein the moveable member and the housing cause the moveable member to rotate when the moveable member moves upwardly upon insertion of the vial, the moveable member returning to a third locked position upon removal of the vial, the third locked position being such that a further vial cannot be inserted into the housing, the first transfer member end being connectable to the second adaptor end, the second transfer member end being arranged to receive a neck of a vial.

The syringe utilized in the present invention may be of the conventional type. Thus, the syringe would have a first end with a needle located thereat with a second opened end. A plunger is mounted within the syringe to contain the material therein in a conventional manner. The needle may be of the staked-in type—i.e. permanently fixed to the end and communicating with the interior of the syringe.

The transfer arrangement also includes an adaptor with a first end of the adaptor being designed to connect to the syringe end having the needle. The adaptor extends about the needle to prevent access thereto. This is a safety measure to prevent accidental pricking. The opposite adaptor end preferably has a luer connection.

When not in use, the transfer arrangement also preferably includes a tip cap which fits within the adaptor end having the luer connector.

The transfer arrangement also includes a transfer member which has first and second transfer member ends, the first transfer member end being connectable to the adaptor end after removal of the tip cap, the second transfer member end being designed to receive the neck of a vial.

As is utilized in most syringe arrangements, there is provided a plunger rod which is connectable to the plunger. For operational purposes, there is preferably also provided a back stop connected to the syringe proximate the first syringe for aiding in the movement of the plunger rod.

BRIEF DESCRIPTION OF THE DRAWINGS

Having thus generally described the invention, reference will be made to the accompanying drawings illustrating an embodiment thereof, in which:

FIG. 4 is a cross sectional view of the transfer device prior to its use;

FIG. 5 is a side sectional view of the device being placed on a vial;

FIG. 6 is a side sectional view showing piercing of the vial;

FIG. 7 is a cross sectional view illustrating the cap being removed;

FIG. 13 is a cross sectional view illustrating placement of the transfer assembly on a vial;

FIG. 14 is an exploded view illustrating the transfer assembly and the vial prior to insertion of the vial;

FIG. 15A is a bottom perspective view of a transfer assembly according to one embodiment of the present invention;

FIG. 15B is a bottom plan view thereof;

FIG. 16A is a perspective view of the transfer assembly according to a further embodiment;

FIG. 16B is a bottom plan view thereof;

FIG. 17A is an exploded view of the transfer assembly;

FIG. 17B is a bottom perspective view thereof;

FIGS. 17C to 17E show the sequence of placing the transfer assembly on the vial;

FIGS. 17F to 17H illustrate the placement of the transfer assembly in a further embodiment thereof on a vial;

FIG. 18 is an exploded view of the transfer assembly; and

FIGS. 21 to 28 illustrate use of the system of the present invention.

DETAILED DESCRIPTION OF THE INVENTION

Figure 1:
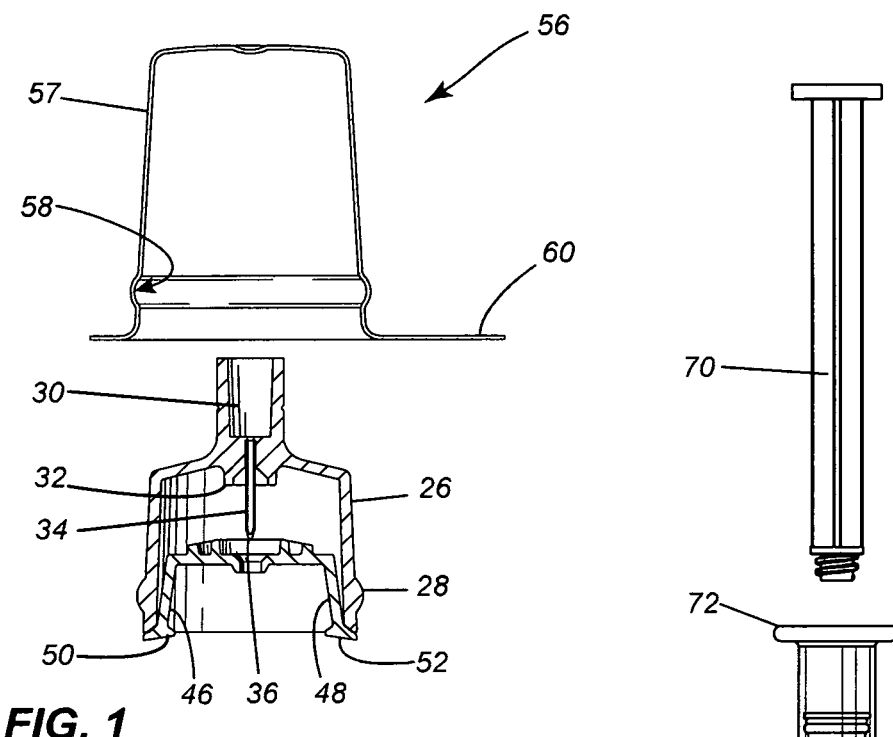
FIG. 1 is a side elevational view of a transfer device according to the present invention.
Figure 2:
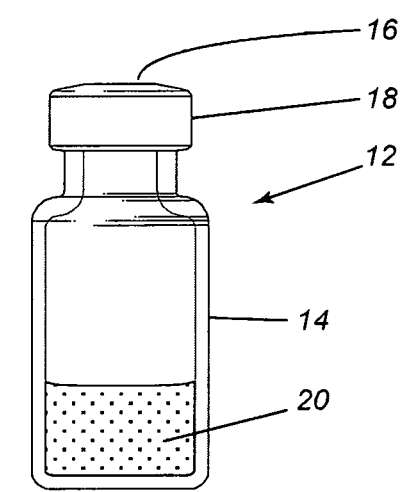
FIG. 2 is a side elevational view, partially in section, of a vial containing a medicant.
Figure 3:
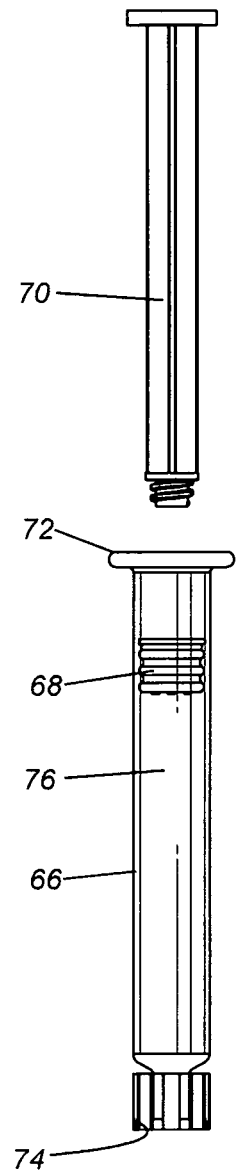
FIG. 3 is a side elevational view of a syringe and plunger rod.

Referring to the drawings in greater detail and by reference characters thereto, there is illustrated a transfer system which is generally designated by reference numeral 10 and which is suitable for use with a vial generally designated by reference numeral 12.

Vial 12 has a body 14 with a neck sealed by a septum 16 over which there is a cap 18. A medicant 20 is contained within body 14 and would typically comprise a dry ingredient although a fluid may also be utilized.

Transfer system 10 includes an outer housing 24 and a circular side wall 26. On circular side wall 26 there is a protrusion 28 near the bottom thereof. On its upper end, there is provided a luer connection 30. An inner wall 32 mounts a needle 34 which is hollow in nature and has a piercing end 36. As previously mentioned, needle 34 may be a spike.

Mounted interiorly of outer housing 24 is a moveable member 40. Moveable member 40 has a top wall 42 with an aperture 44 centrally located therein to permit the passage of needle 34. Extending downwardly from top wall 42 is a first leg 46 and a second leg 48. First leg 46 has an outwardly extending flange 50 at the bottom thereof while second leg 48 also has an outwardly extending flange 52.

A cover 56 is provided to receive transfer system 10. Cover 56 has a side wall 57 which is adapted to engage with protrusion 28 to retain transfer system 10 in position. Side wall 57 is provided with an outwardly extending flange 60 at the bottom thereof. Flange 60 is designed to receive a peelable sealing strip 62 so as to provide a hermetically sealed package.

The transfer system of the present invention is preferably utilized with a syringe which has a syringe body 66 and a plunger 68 mounted therein. A plunger rod 70 is designed to be screwthreadably engageable with plunger 68. Syringe body 66 includes a backstop 72 to permit proper gripping by the hand of a user. At its front end, syringe body 68 includes a luer connector 74. Typically, syringe body 66 is filled with a diluent 76 although any desired fluid may be utilized.

Figure 8:
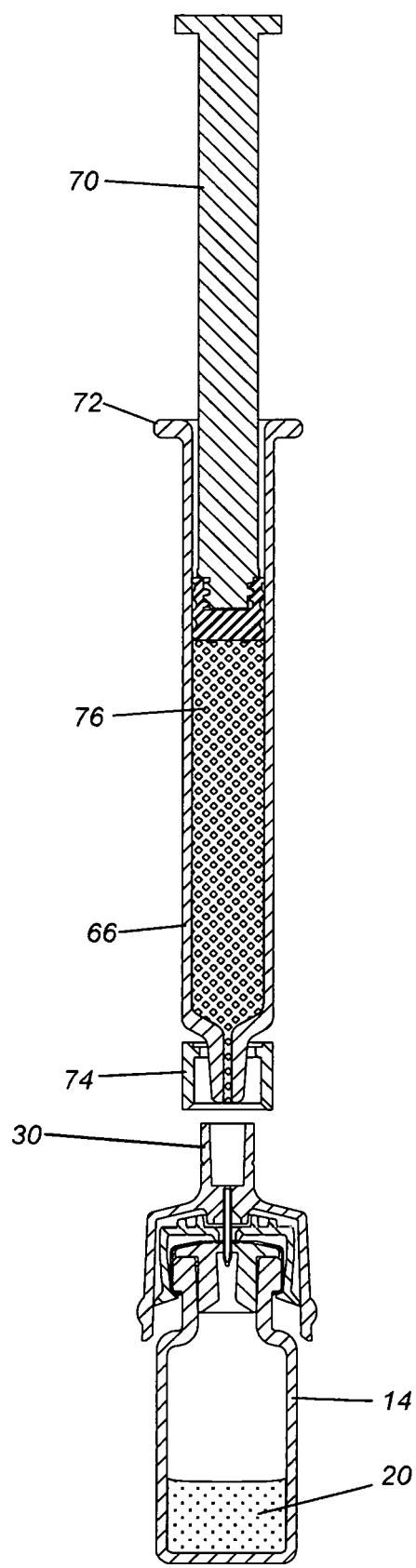
FIG. 8 is a cross sectional view illustrating a luer lock syringe being ready to be placed on the vial.
Figure 9:
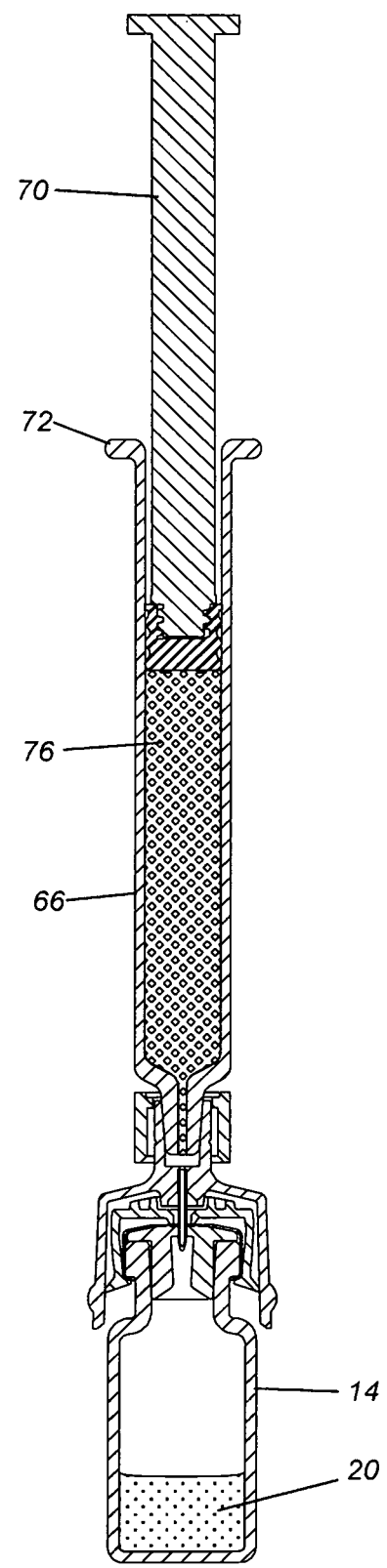
FIG. 9 is a view, partially in cross section, of a luer lock syringe being attached to the transfer device.
Figure 10:
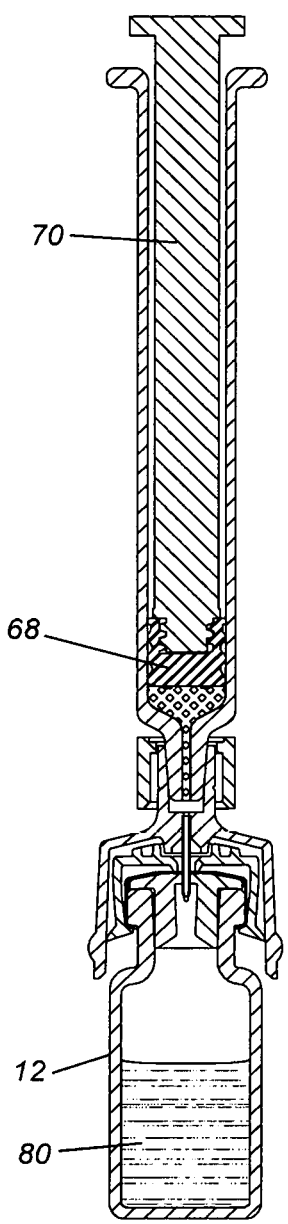
FIG. 10 is a sectional view illustrating the mixing of components.
Figure 11:
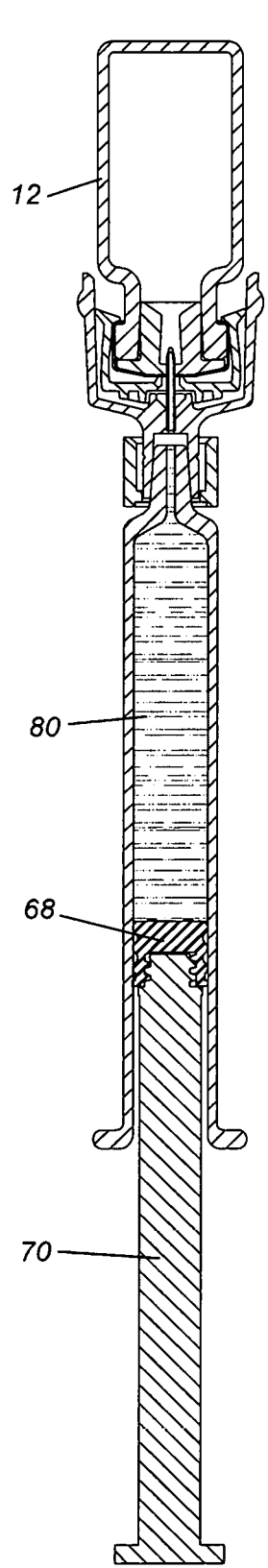
FIG. 11 is a sectional view illustrating the aspiration of the mixture into the syringe.
Figure 12:
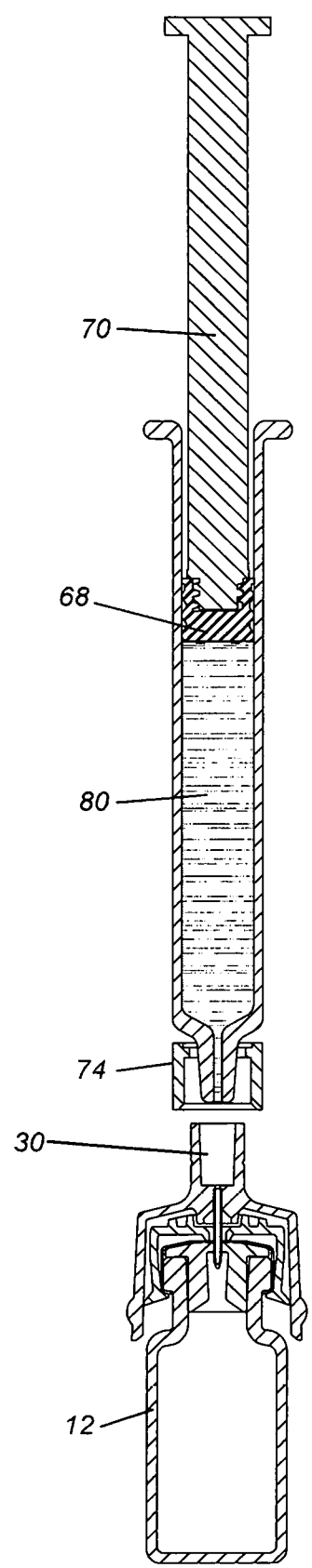
FIG. 12 is a sectional view showing the syringe being detached.

As shown in FIGS. 8 and 9, plunger rod 70 is connected to plunger 68 and the diluent 76 is then forced into vial body 14 as shown in FIG. 10. The medicant and diluent may then be mixed and the assembly inverted as shown in FIG. 11. The mixture 80 is then aspirated back into syringe body 66. The mixture 80 is then ready for injection when a needle assembly is connected to luer connector 74.

In the embodiment of FIGS. 17A to 17H, it will be noted that outer housing 24 is provided with a pair of apertures 86 in side wall 26. Also, in this embodiment, there are provided an extra pair of legs 87 each having buttons 88 formed on an exterior surface thereof. In this embodiment, when the moveable member 40 moves upwardly, buttons 88 engage in apertures 86.

On the interior surface of wall 26, there are provided ribs 90 which have a groove 92 formed therein. Thus, when pressure is exerted on buttons 86 as vial 12 is being withdrawn, moveable member 40 will move downwardly until the top wall 42 engages with groove 92. This retains moveable member 40 in position for further use.

Figures 19A, 19B:
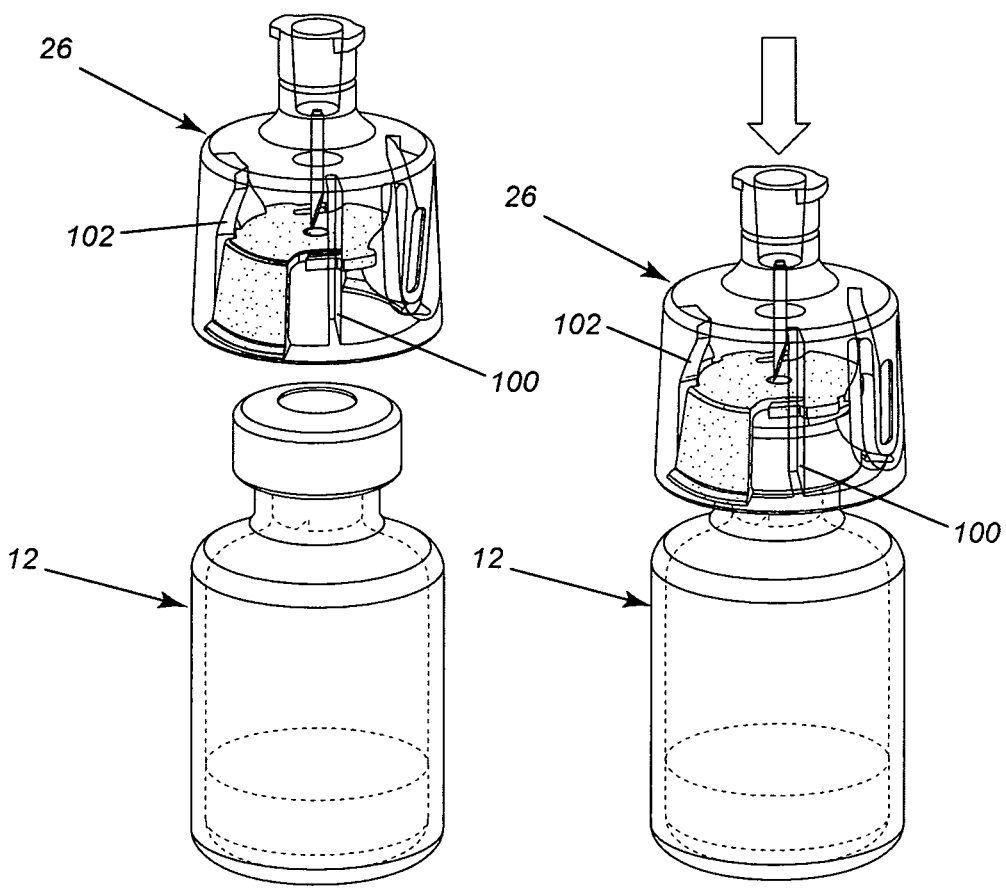
FIGS. 19A to 19D are perspective views illustrating placement of the transfer assembly on a vial and removal thereof.
Figures 19C, 19D:
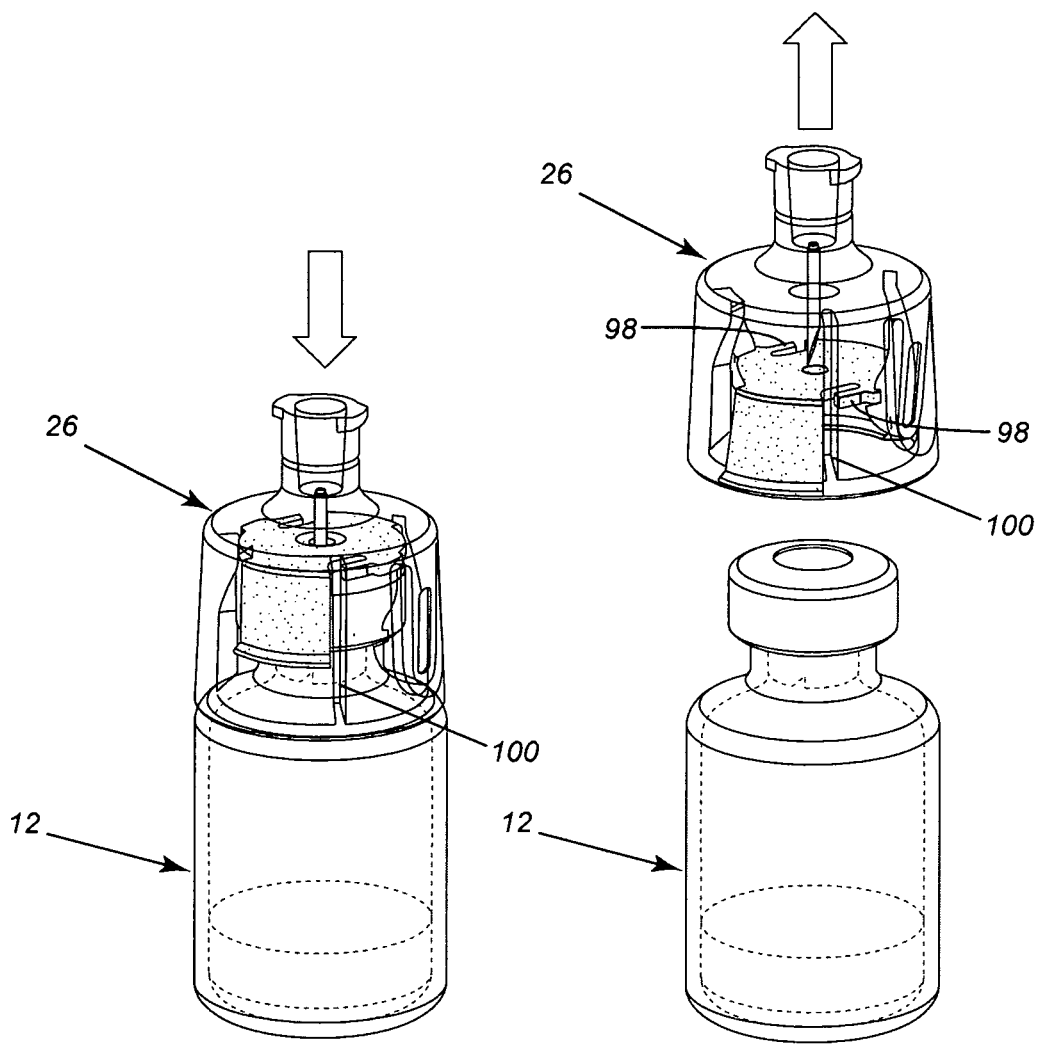

In the embodiment of FIGS. 18 to 19D, it will be noted that top wall 42 is provided with protrusions 96 and locking latches 98. On the interior there are provided ribs 100 and angled side wall portions 102. The arrangement is such that upon upward movement of moveable member 94, protrusions 96 engage with angled side wall 102 to rotate moveable member 40. Upon withdrawal, locking latches 98 engage with rib 100 so as to prevent further use of the transfer member.

Figure 20:
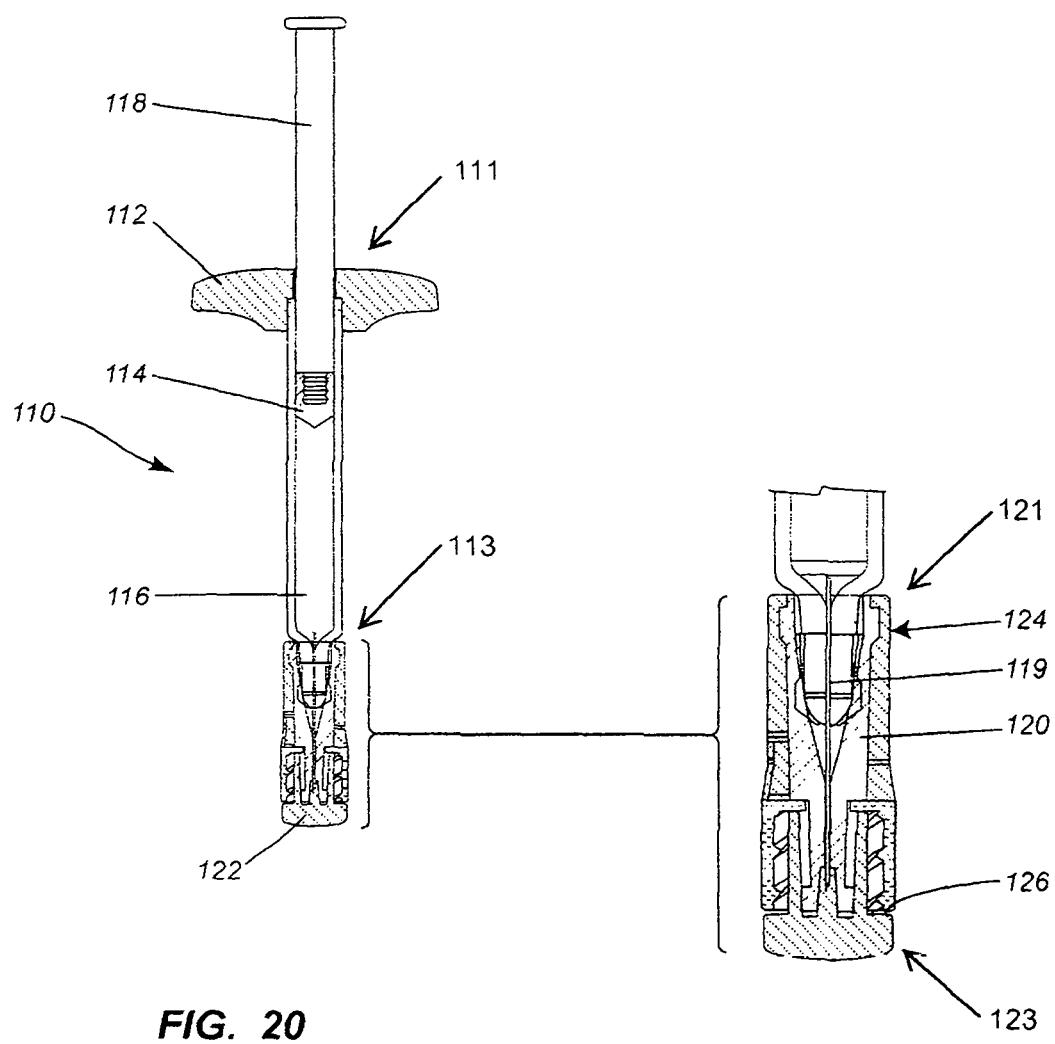
FIG. 20 is a view of a staked-in needle syringe using the concept of the present invention.

As shown in FIG. 20, the present invention utilizes a syringe generally designated by reference numeral 110. Syringe 110 is provided with a back stop 112 as is known in the art. A plunger 114 seals a first syringe end 111 and defines a compartment 116 which will contain the liquid diluent. A plunger rod 118 is used to advance plunger 114 when required.

At the second end forming the injection end 113, there is provided a staked-in needle 119 and a needle shield 120. A tip cap 122 extends over needle 119.

An adaptor generally designated by reference numeral 124 has first and second ends 121, 123 respectively with an internal luer connector 126 being located at second adaptor end 123.

In operation, and as shown in FIGS. 21 to 28, there is provided a transfer member 128 as previously described in FIGS. 1 to 19 and which has first and second transfer member ends 131 and 133. A vial 130 contains the dry component 135 to be mixed with the liquid in compartment 116 of syringe 110.

Initially, transfer system 128 is placed over the top of vial 130 as shown in FIG. 22. Subsequently, tip cap 122 is removed. As seen in FIG. 24, transfer system 128 is then connected via luer connector to syringe 110. As shown in FIG. 25, the reconstitution is then begun with initial downward movement to transfer the liquid into vial 130 and subsequent aspiration to bring the mixture back into syringe 110.

Figures 27, 28:
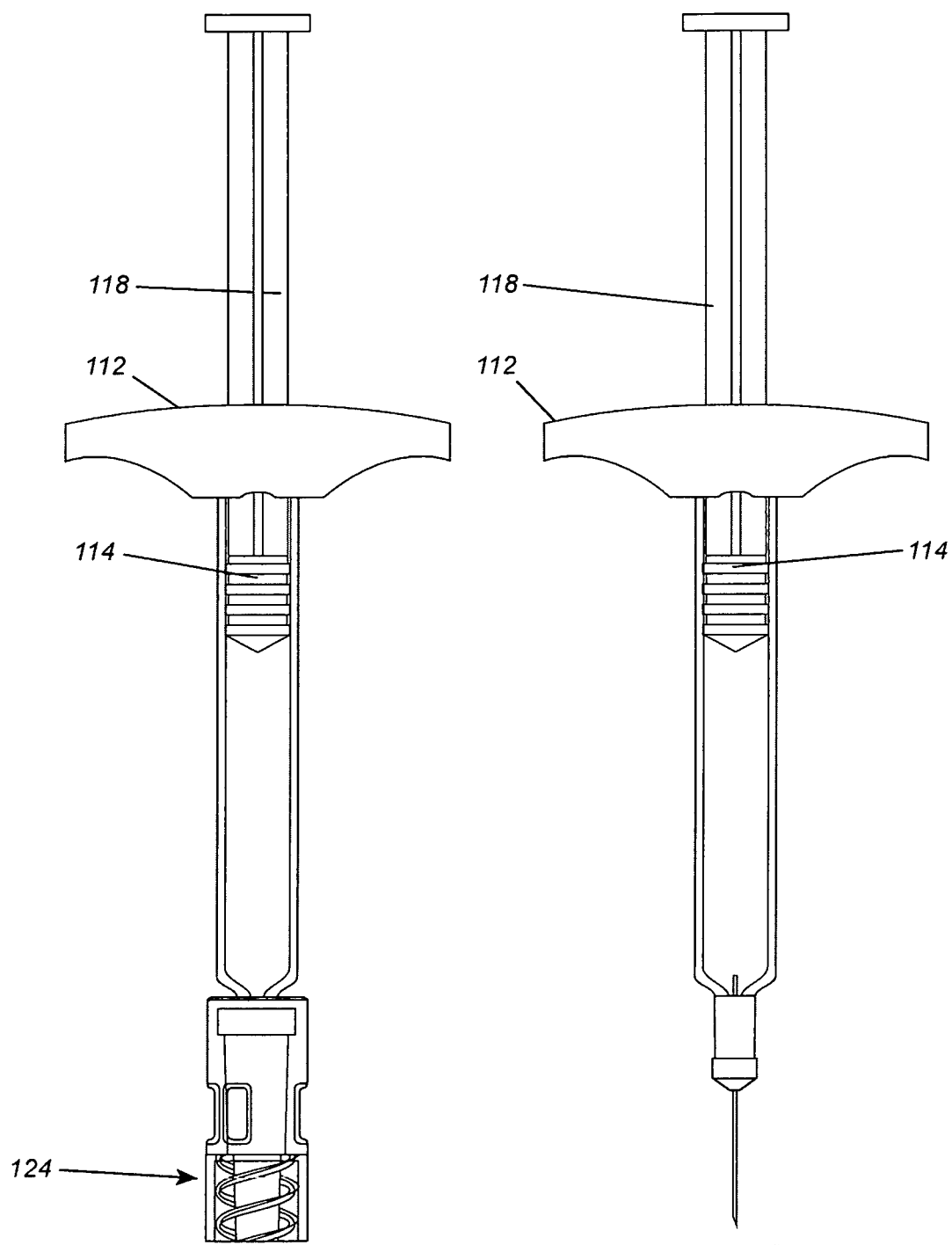

Subsequently, as shown in FIG. 26, the vial and transfer system 128 are disconnected and then, as shown in FIG. 28, syringe 110 is ready for injection of its contents.

Using the above system, the needle used for injection is protected at all times. Thus, there is no risk of damage to needle 119 nor to the possibility of contaminates entering the system.

It will be understood that the above described embodiment is for purposes of illustration only and changes and modifications may be made thereto. Thus, one could use other vial adaptors and one need not necessarily use a cap.

We claim:

1. A transfer device comprising:
    a housing (24) having a top, a side wall (26), an open bottom, said open bottom permitting insertion of a vial (12) within said housing;
    a piercing member (34) mounted within said housing (24), said piercing member (34) having a piercing tip (36) located at a bottom end thereof, said piercing member having an interior passageway formed therein;
    a connector (30) located on an exterior side of said top;

a moveable member (40) mounted within said housing (24), said moveable member (40) being moveable from a first position wherein said moveable member (40) prevents access to said piercing tip (36) to a second position permitting access to said piercing tip when said vial is inserted in said housing;

a transfer member (128), said transfer member (128) having first and second transfer member ends (131, 133) wherein said moveable member (40) and said housing (24) cause said moveable member (40) to rotate when said moveable member (40) moves upwardly upon insertion of said vial (12), said moveable member returning to a third locked position upon removal of said vial, said third locked position being such that a further vial cannot be inserted into said housing, said first transfer member end (131) being connectable to said second adaptor end (123), said second transfer member end (133) being arranged to receive a neck of a vial (130).

2. The transfer device of claim 1 wherein said moveable member includes at least one leg (46), said housing having a recess formed therein, said leg engaging said recess when said moveable member is in said second position, said moveable member being returnable to said first position upon removal of said vial by pressure on said leg to release said leg from said recess.

3. The device of claim 1 wherein said piercing member (34) is selected from the group consisting of a needle or spike.

4. The device of claim 3 wherein said moveable member (40) has a centrally located aperture (44) to permit said piercing member (34) to pass therethrough.

5. The device of claim 1 wherein said connector (30) on the exterior side of said top comprises a luer connector.

6. The device of claim 2 wherein said moveable member (40) has two projections, each projection being located on a respective one of diametrically opposite legs.

7. The device of claim 6 wherein said housing (24) has a recess formed on an interior surface thereof to receive a disc portion of said moveable member (40) when said moveable member is in said first position.

\* \* \* \* \*